US007752178B2

(12) United States Patent
Anderson

(10) Patent No.: US 7,752,178 B2
(45) Date of Patent: Jul. 6, 2010

(54) METHOD TO INDICATE CONTEXT SYNCHRONIZATION OF APPLICATIONS ON A COMPUTER DESKTOP

(75) Inventor: Michael J. Anderson, Surrey (CA)

(73) Assignee: McKesson Information Solutions LLC, Alpharetta, GA (US)

(*) Notice: Subject to any disclaimer, the term of this patent is extended or adjusted under 35 U.S.C. 154(b) by 409 days.

(21) Appl. No.: 11/215,479

(22) Filed: Aug. 30, 2005

(65) Prior Publication Data

US 2007/0050359 A1  Mar. 1, 2007

(51) Int. Cl.
G06F 17/00 (2006.01)

(52) U.S. Cl. ...................................... 707/690
(58) Field of Classification Search ........................ None
See application file for complete search history.

(56) References Cited

U.S. PATENT DOCUMENTS

| 6,041,066 | A | 3/2000 | Meki et al. | |
|---|---|---|---|---|
| 6,212,247 | B1 | 4/2001 | Olafsson | |
| 6,233,606 | B1 | 5/2001 | Dujari | |
| 6,493,748 | B1 | 12/2002 | Nakayama et al. | |
| 6,691,588 | B2 | 2/2004 | Miyazaki et al. | |
| 6,718,361 | B1 | 4/2004 | Basani et al. | |
| 6,748,447 | B1 | 6/2004 | Basani et al. | |
| 6,754,699 | B2 | 6/2004 | Swildens et al. | |
| 6,778,493 | B1 | 8/2004 | Ishii | |
| 6,889,363 | B2 | 5/2005 | Maloney | |
| 6,912,707 | B1 * | 6/2005 | Fontes, Jr. | 717/113 |
| 2002/0107875 | A1 * | 8/2002 | Seliger et al. | 707/200 |
| 2003/0105642 | A1 * | 6/2003 | Andino et al. | 705/1 |
| 2005/0081156 | A1 * | 4/2005 | Clark et al. | 715/736 |
| 2005/0146525 | A1 * | 7/2005 | Widera et al. | 345/440 |
| 2006/0106648 | A1 * | 5/2006 | Esham et al. | 705/3 |
| 2006/0248123 | A1 * | 11/2006 | Butash et al. | 707/201 |
| 2008/0033761 | A1 | 2/2008 | Brummel et al. | |

FOREIGN PATENT DOCUMENTS

WO    WO0059286    10/2000

OTHER PUBLICATIONS

Office Action dated Mar. 20, 2009, Canadian Patent Application No. 2,558,692, filed Aug. 30, 2006.

* cited by examiner

Primary Examiner—Don Wong
Assistant Examiner—Belinda Xue
(74) Attorney, Agent, or Firm—Alston & Bird LLP

(57) ABSTRACT

The present disclosure is directed to a method to indicate context synchronization of applications on a computer desktop that polls information from disparate applications and provides an indication of whether or not the information is synchronized. The disclosure uses an application located on each workstation that performs the "polling" and displays the synchronization state. The present disclosure does not involve a server process. Because of the rules governing abstracts, this abstract should not be used to construe the claims.

39 Claims, 10 Drawing Sheets

METHOD TO INDICATE CONTEXT SYNCHRONIZATION OF APPLICATIONS ON A COMPUTER DESKTOP

BACKGROUND OF THE INVENTION

The present invention is directed to a method for determining and indicating context synchronization of disparate applications running on a computer. The invention utilizes a single user interface to indicate whether disparate applications running on a computer display information related to the same context or entity, for example, a patient.

In the healthcare industry, a user, such as a healthcare worker, clinician, physician, technician, nurse, etc. routinely uses a computer to view multiple computer applications relating to various patients. The computer provides easy access to medical records contained in various computer applications for patients that are conveniently accessed through a computer workstation. The clinician oftentimes reviews various medical records of a patient contained in multiple, disparate computer applications to compare and correlate the data. Each application may display different information about a patient or entity. The information contained in disparate applications is oftentimes reviewed and aggregated by the user who may be, for example, attempting to diagnose a patient.

However, because of the ease with which a user may change between entities, the possibility exists that the user may be viewing information in one application for one patient and information in another application for a different patient. If the user does not realize that the information being viewed in the disparate applications are for different patients, a catastrophic error could occur such as misdiagnosis. Therefore, patient safety is at stake. Additionally, if each application displays data for a different entity or patient, the user's decision based on the aggregate data is meaningless.

Therefore, there is a need to provide an easy and accurate method for determining and indicating context synchronization of disparate applications running on a computer. This problem has existed ever since users started correlating data displayed amongst multiple simultaneously running applications.

Currently, three solutions exist to deal with this problem. The first is a manual approach. That is, the user must remember to carefully check each application to ensure that the applications are displaying information for the same entity of interest prior to using the information. Obviously, this manual approach is error-prone. The user must remember to check each application before aggregating and using the information displayed by the applications.

The second approach is an automated approach. That is, for select applications that implement a Clinical Context Object Workgroup ("CCOW") or CCOW-like synchronization protocol, users rely on those applications to automatically synchronize. The disadvantages of this approach will be discussed further below. The third approach is a combination of manual and automated. That is, when a combination of applications that understand CCOW or CCOW-like protocols are used on the same desktop as applications that do not. The manual aspect of this approach has the same disadvantages as described above. The disadvantages with respect to the automated aspect of this approach are described below.

More specifically, the CCOW protocol (or CCOW-like synchronization protocol) supports synchronizing the applications for a selected patient. When the user of an application changes the selected patient, the other applications on the workstation follow the change automatically. This cooperation frees the user from repeating the change action in more than one application.

The CCOW protocol requires applications to notify a manager application when the application is going to change its context (or entity or patient). Additionally, the CCOW protocol requires applications to display an icon, located somewhere inside the application, to indicate the synchronization state. Further, the CCOW protocol requires the use of notification messages sent from the manager application to the participant applications to force the applications to update their state when context (or entity or patient) changes. In this way, all applications display the same context. Part of the notification mechanism involves having participant applications display a dialog to the user to allow the user to choose whether or not to cause the application to break-away/leave the context. This dialog would be displayed when an application has an "unsaved data condition" and the application can not be forced into changing its context because of a chance for data to be lost. Finally, the CCOW protocol requires additional programming typically done so a participant application can communicate with the managing application, that is, so that the participant application can notify the manager when its context has changed and receive notifications from the manager that context has changed.

However, the need exists for a single user interface to indicate whether disparate applications running on a computer display information related to the same entity in a more simplified and elegant manner. That is, the need exists for a single user interface that polls information from disparate applications and provides an indication of whether or not information is synchronized.

SUMMARY

This disclosure uses an application located on each client workstation that performs the "polling" and displays the synchronization state. The present disclosure does not involve a server process, and the applications to be "watched" may be preconfigured. This disclosure utilizes a single user interface to indicate whether disparate applications running on a computer display information related to the same entity, or context or patient. When all applications have the same context, context is synchronized. The Context synchronization state may be synchronized, not synchronized, or indeterminate.

One aspect of the present disclosure uses color and/or an icon as the computer application's user interface to signify to the user whether or not applications are displaying information related to the same entity. The computer application's user interface (or synchronization indicator or indicator or result) is always available and visible in a consistent location, for example, in the top-right corner of a user's computer desktop, to provide continuous feedback to the user. At any time the user interface color and/or icon may be easily recognizable. Therefore, with a single glance, a user can quickly identify whether or not applications are displaying information related to the same entity, that is synchronized information.

Another aspect of the present disclosure is directed to a method of periodically polling applications for information that the applications are displaying. The present disclosure compares the information from each application, and determines an appropriate color and/or icon to display. A variety of techniques can be used to interface the indicator with the applications to be polled. In most cases, the polling will not interrupt what the application is doing. The polling will attempt to analyze the information being displayed in an application without directly contacting the application. That is, the present disclosure will watch or mine for textual information that the application(s) display, for example, in their windows or that is rendered to their title bars. If this indirect communication is not possible, the indicator may directly contact applications for the information being displayed.

Another aspect of the present disclosure is directed to a method comprising, retrieving identifying information from at least two computer applications, comparing the identifying information, and displaying a result indicative of the comparing.

Another aspect of the present disclosure is directed to a method for indicating context synchronization of applications on a computer comprising, reading a configuration file to determine at least two applications, reading a configuration file to determine identifying information to retrieve from the at least two applications, retrieving identifying information from the at least two applications, comparing the identifying information, and displaying a result in response to the comparing.

Another aspect of the present disclosure is directed to a computer readable medium carrying a set of instructions which, when executed, perform a method comprising, retrieving identifying information from at least two computer applications, comparing the identifying information, and displaying a result indicative of the comparing.

BRIEF DESCRIPTION OF THE DRAWINGS

For the present disclosure to be easily understood and readily practiced, the present disclosure will now be described, for purposes of illustration and not limitation, in conjunction with the following figures, wherein.

DETAILED DESCRIPTION OF THE INVENTION

The current disclosure "watches" or "polls" or "mines" particular preconfigured applications and determines and provides an indication to the user as to whether the applications are displaying data for the same entity, patient, context. The disclosure has three (3) states that the applications may be in, specifically, synchronized, not synchronized and indeterminate. A synchronized state occurs when all configured applications are displaying both critical and non-critical data for the same entity. A not synchronized state occurs when one or more configured applications are displaying critical data for different entities. An indeterminate state occurs when all configured applications are displaying critical data for the same entity, however, non-critical data is different in one or more of the applications.

The disclosure encompasses a software program that actively polls configured applications for specific pieces of data. Once the data has been retrieved from each application, the data is compared to determine which state the disclosure application should transition to and display. The disclosure application must be told which applications it should poll, that is, the applications must be preconfigured. When launched, the disclosure application determines which applications it should retrieve identifying information from by, for example, reading a configuration file. The disclosure application must also be told which pieces of data, for example, patient medical record number (MRN), last name, it should retrieve from each application and how to retrieve that data. This information may also be determined by reading a configuration file or script. The pieces of data may be retrieved by direct interface (e.g. COM) or indirect interface (e.g. screen scraping).

The data is defined to be either critical or non-critical. By default, all data is defined to be critical. The disclosure may be implemented as a software solution or as a combined software and hardware solution.

In one embodiment of the software solution, a disclosure application communicates with predetermined preconfigured applications to determine if those applications are displaying data for the same entity. The computer application's user interface (or indicator or synchronization indicator or result) visually indicates the state of the applications. This may be done by using color and/or an icon located in a consistent location on the user's computer desktop.

In one embodiment of the combined software and hardware solution, a disclosure application communicates with predetermined applications to determine if those applications are displaying data for the same entity. The disclosure application may then communicate to hardware which visually indicates the state of the applications, for example, by using a colored LED as the indicator.

Figure 1:
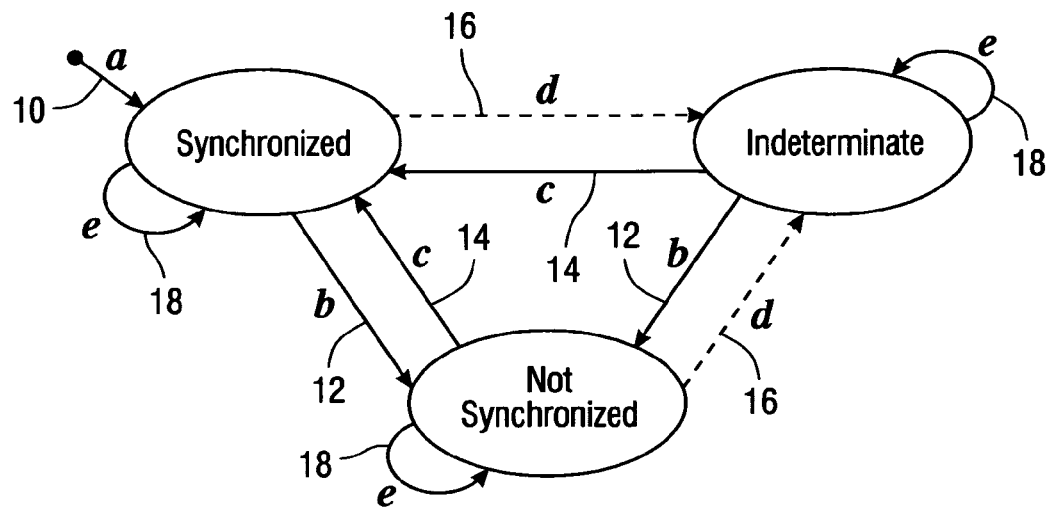
FIG. 1 is a diagram depicting the context synchronization states of the applications and transitions to and from those states.

FIG. 1 is a diagram depicting the context synchronization states and transitions to and from those states. As depicted by "a" 10, the initial state is synchronized. Typically, the disclosure application will be launched as one of the first programs on a computer. As depicted by "b" 12, the state becomes not synchronized when, after retrieving data from each application, comparison of critical data reveals one or more applications are not displaying the same data values. As depicted by "c" 14, the state becomes synchronized when, after retrieving data from each application, comparison of the critical and non-critical data reveals that all applications are displaying the same data values. As depicted by "d" 16, the state becomes indeterminate when, after retrieving data from each application, comparison reveals all applications are displaying the same critical data values, and one or more applications are not displaying the same non-critical data values. This indeterminate state may only be reached if the application has been configured to retrieve and compare non-critical data values. As depicted by "e" 18, the state remains in its previous state if, after retrieving data from each application, comparison reveals the same result as the previous comparison. In one embodiment, the disclosure application is designed to poll or retrieve and compare data from each application every two (2) seconds.

The following pseudo code describes the disclosure application:

```
Forever
    Sleep (2 seconds)                    // poll every 2 sec
    Foreach application i
        data[i] = getContext(i)          // poll app state
    state = compareContexts(data[ ])
    displayState(state)                  // update indicator
getContext -
input: application to poll
output: an application's context; the data values displayed in an application
that were configured to be retrieved
```

This is a rich function that can retrieve an application's context through a variety of means. Some interface is required to the application, whether it is direct interface (e.g. COM) or indirect interface (e.g. screen scraping).

compareContexts— input: 1 to n application contexts output: one of the following states—synchronized, not synchronized, indeterminate This function compares the input context to each other, and outputs a single result—the state the application should transition to. This function must take into consideration whether data values were configured to be critical or non-critical. A specialization of the synchronized state may be returned (that is, the "prior report being viewed" synchronized state) if the "prior report being viewed" scenario is observed; that is, if all applications are displaying synchronized contexts except for applications that can display historical or prior report information and are displaying historical or prior report information for the same patient which is being displayed in all other synchronized applications. Applications may be pre-configured as being able to display historical or prior report information; and are deemed to be displaying historical or prior report information when displayed critical data values are synchronized but non-critical data values are not, (that is, the application that can display historical or prior report information displays the same patient MRN and last names (critical data) as the other synchronized applications, but different study accession numbers (non-critical data)).

displaystate— input: the state the application should transition to output: state is visually displayed to the user This function visually indicates the input state to a user via an indicator. In a software solution, this may involve rendering a new icon to the disclosure application's user interface that is an appropriate color and/or picture (icon) to indicate the input state. If a hardware solution is involved, this may involve turning on an appropriate colored LED to indicate the input state.

Figure 2:
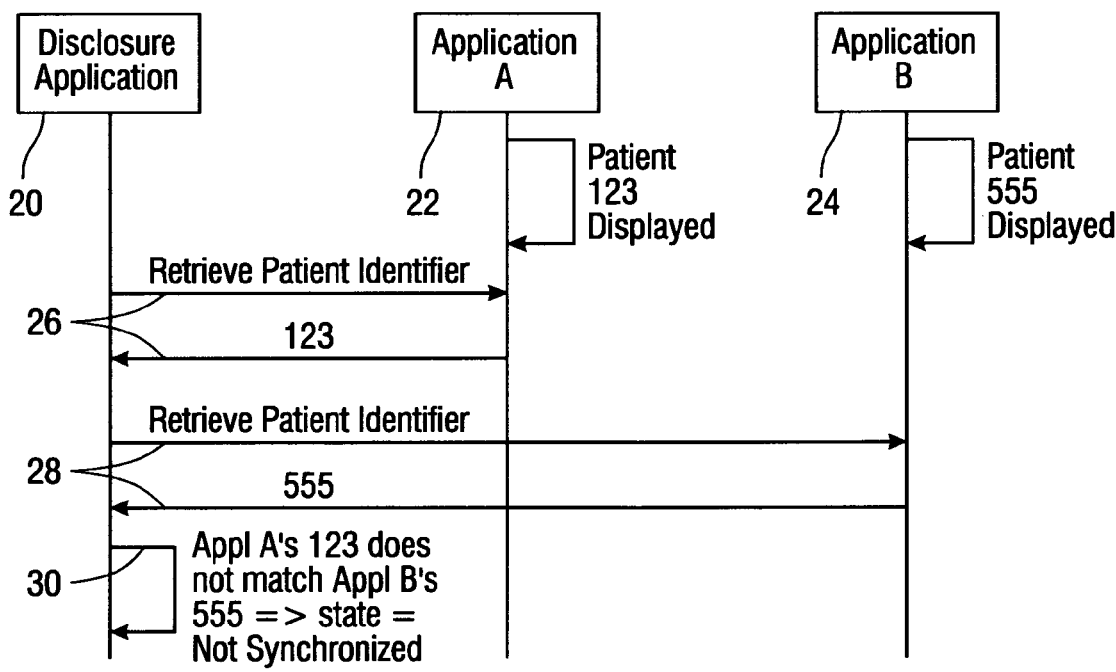
FIG. 2 depicts a sequence diagram illustrating a sample scenario of the dynamics of the present disclosure application.

FIG. 2 depicts a sequence diagram illustrating a sample scenario of the dynamics of the present disclosure application. More specifically, FIG. 2 shows an example of the disclosure application 20 interaction with two preconfigured applications, that is, Application A, 22 and Application B, 24. Application A, 22 displays information pertaining to a particular patient, for example, Patient 123. Application B, 24 displays information pertaining to another patient, for example, Patient 555. Disclosure application 20 at step 26 retrieves patient identifier information from Application A, 22, that is, that Application A, 22 displays information pertaining to Patient 123. Disclosure application 20 at step 28 retrieves patient identifier information from Application B, 24, that is, that Application B, 24 displays information pertaining to Patient 555. Disclosure application 20 at step 30 compares the information retrieved from Application A, 22 with the information retrieved from Application B, 24 and notes that Patient 123 and Patient 555 do not match. Disclosure application 20 determines that the state is therefore not synchronized.

Figure 3:
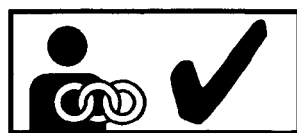
FIG. 3 illustrates one embodiment of an indicator displayed when context is synchronized, specifically one embodiment of a "linked" indicator.

FIG. 3 illustrates one embodiment of an indicator displayed when context is synchronized, specifically one embodiment of a "linked" indicator 32. As previously discussed, the indicator or computer application's user interface will display a different status to the user based on a comparison of the context in each visible application. The "linked" indicator 32 indicates the synchronized state, that is, when all applications have the same context the context is "linked". In one embodiment the "linked" indicator 32 may be visible in the color green. The "linked" indicator 32 in another embodiment may show a "check" mark. Additionally, in another embodiment, the "linked" indicator 32 may be visible in the color green and may show a "check" mark. Any number of color choices or icons may be used to indicate the "linked" indicator 32. Various types of information (icons, links, color, etc.) may be used to relate status information to the user.

Figure 4:
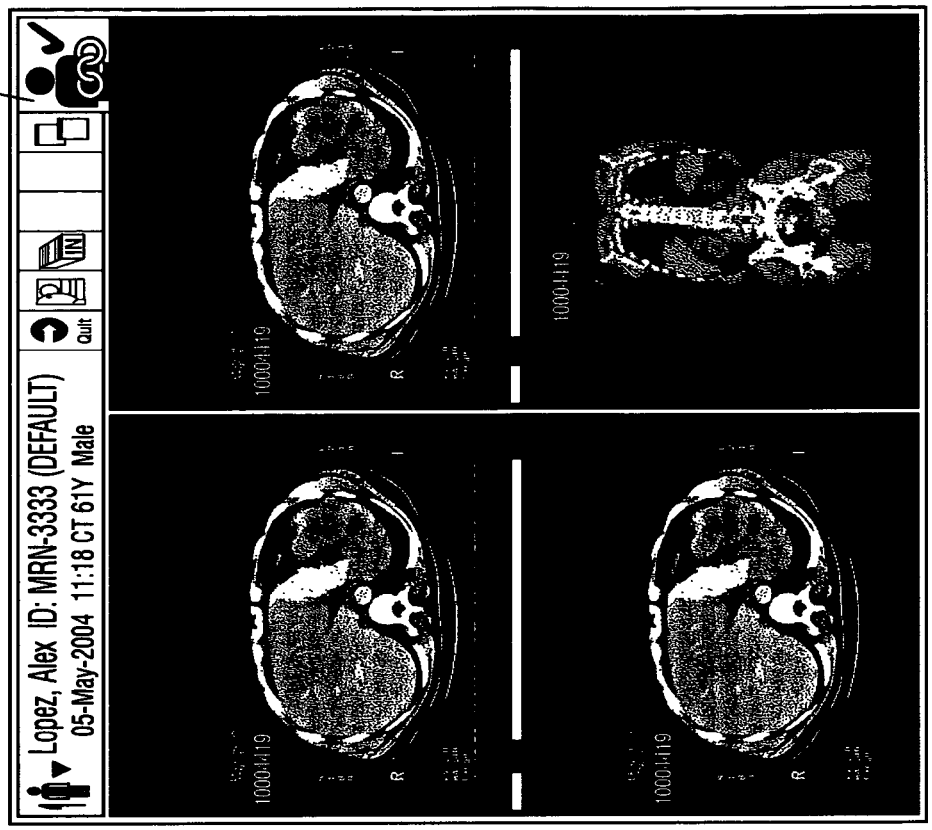
FIG. 4 illustrates screen shots of one embodiment showing two applications on a computer desktop that are synchronized with the "linked" indicator in the top right-hand corner displaying the synchronized state.
Figure 4:
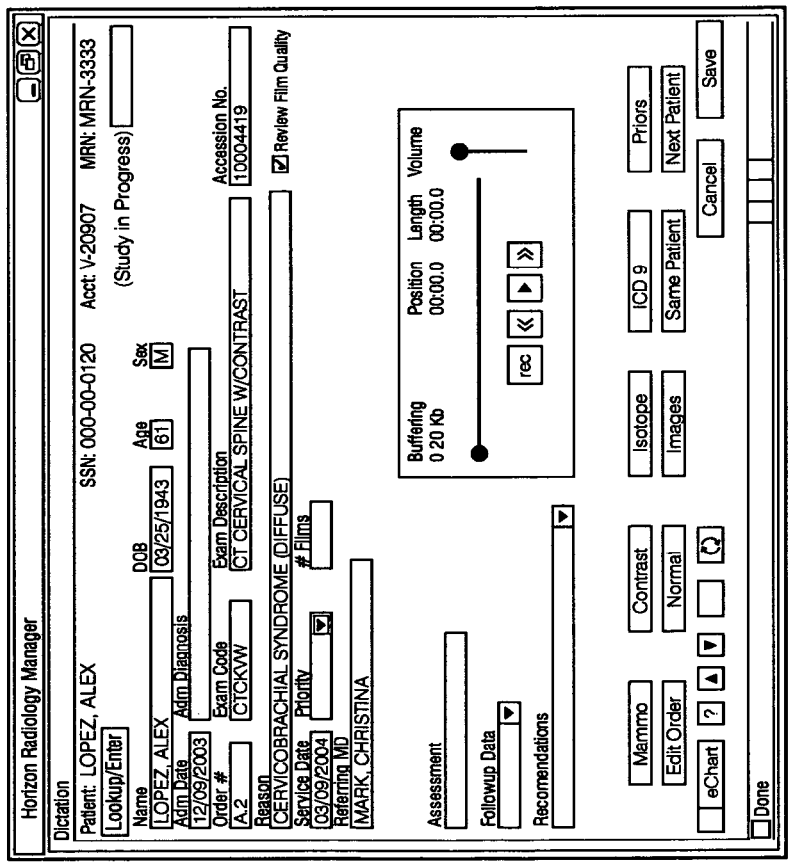

As previously discussed, the "linked" indicator 32 (See FIG. 3) will be displayed when all of the visible applications have synchronized critical and non-critical data. This data may be MRN, last name, and accession number. FIG. 4 illustrates screen shots of one embodiment showing two applications on a computer desktop that are synchronized with the "linked" indicator 32 in the top right-hand corner displaying the synchronized state.

Figure 5:
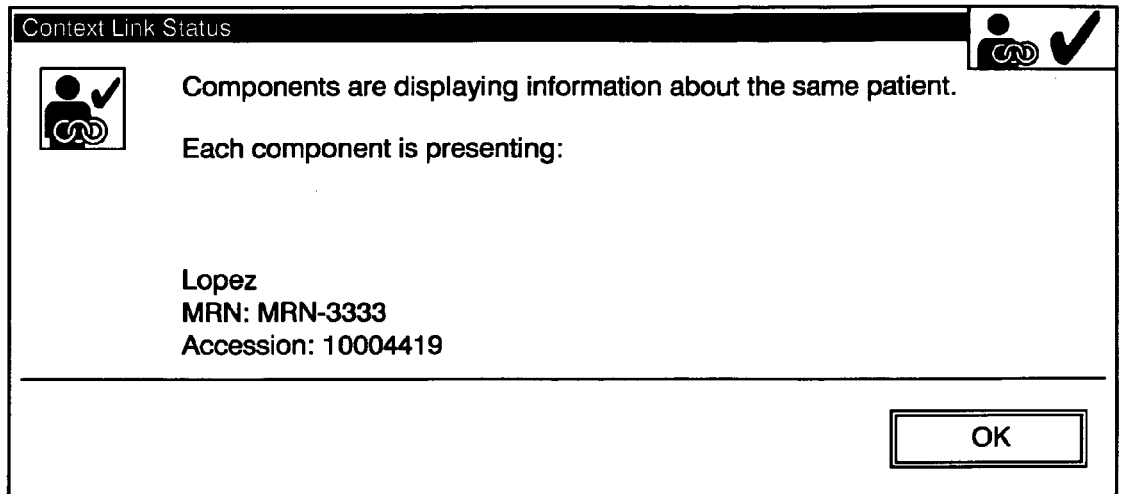
FIG. 5 illustrates one embodiment of a dialog box displaying detailed synchronization state information when all applications are synchronized.
Figure 6:
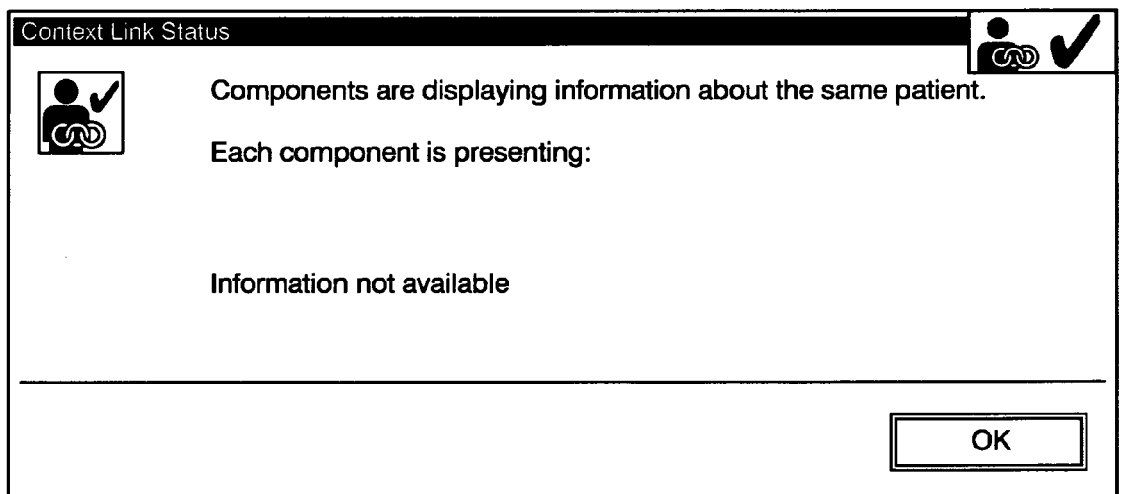
FIG. 6 illustrates one embodiment of a dialog box displaying detailed synchronization state information when no patient information is loaded in any application.

In the current embodiment, it is then possible to double click on the "linked" indicator 32 to display a dialog box (as shown in FIG. 5) explaining the icon status. FIG. 5 illustrates one embodiment of a dialog box 34 displaying detailed synchronization state information when all applications are synchronized. Additionally, if no patient is loaded in any application, the "linked" indicator may still be displayed. FIG. 6 illustrates one embodiment of a dialog box 36 displaying detailed synchronization state information when no patient information is loaded in any application. As shown in FIG. 6, dialog box 36 will indicate that information is not available.

Figure 7:
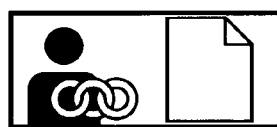
FIG. 7 illustrates one embodiment of an indicator displayed in a scenario when context appears not synchronized, but is in fact synchronized, specifically one embodiment of a "prior report being viewed" indicator.

FIG. 7 illustrates one embodiment of an indicator displayed in a scenario when context appears not synchronized, but is in fact synchronized, specifically one embodiment of a "prior report being viewed" indicator 38. In one embodiment the "prior report being viewed" indicator 38 may be visible in the colors green and yellow. The "prior report being viewed" indicator 38 in another embodiment may show an icon displaying a piece of paper mark. Additionally, in another embodiment, the "prior report being viewed" indicator 38 may be visible in the color green and may also show an icon displaying a piece of paper visible in the color yellow mark. Any number of color choices or icons may be used to indicate the "prior report being viewed" indicator 38.

The "prior report being viewed" indicator 38 may be displayed, for example, when one of the visible applications is displaying a prior report. An example scenario is as follows. The disclosure application may be monitoring, watching or polling three applications, for example, a Rad Report, HRM and HRS. If both HRM and HRS have synchronized MRN, last name and Accession numbers, but in the Rad Report—an application that has the ability to display a prior report, the Accession number is different, the "prior report being viewed" indicator will be displayed.

Figure 8:
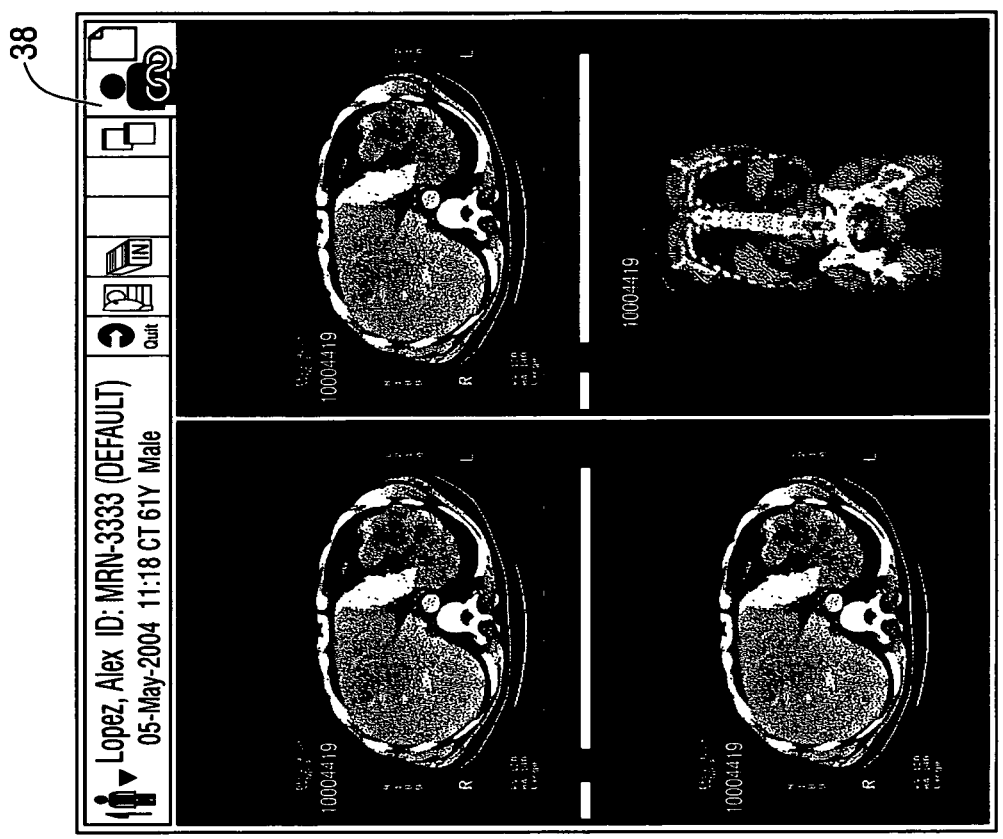
FIG. 8 depicts screen shots of one embodiment showing a "prior report being viewed" indicator as it may appear in the context of the computer screen displaying applications.
Figure 8:
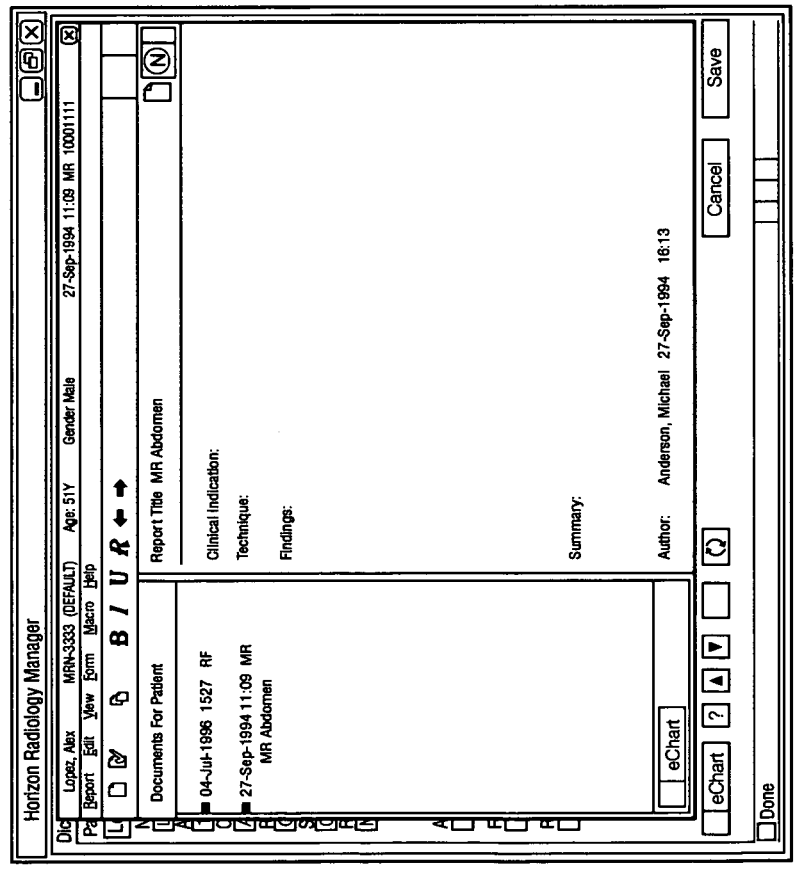

FIG. 8 depicts screen shots of one embodiment showing a "prior report being viewed" indicator 38 as it may appear in the context of the computer screen displaying applications. In the scenario shown in FIG. 8, three applications are visible. One application displays a patient's images from a particular visit. Another application displays the information for that patient's particular visit. The third application displays a report for that patient's previous visit. The patient is the same in all three monitored applications, however, the visit is different. In Radiology, this is a common scenario. To diagnose a patient, historical information regarding that patient's previous visit(s) may be referenced. Because this is a common scenario, this is considered to be a synchronized scenario or state. The "prior report being viewed" indicator 38 is displayed to indicate this state "prior report being viewed" scenario or state. As previously mentioned, the "prior report being viewed" scenario or state is a synchronized state as the patient is the same in all monitored applications.

Figure 9:
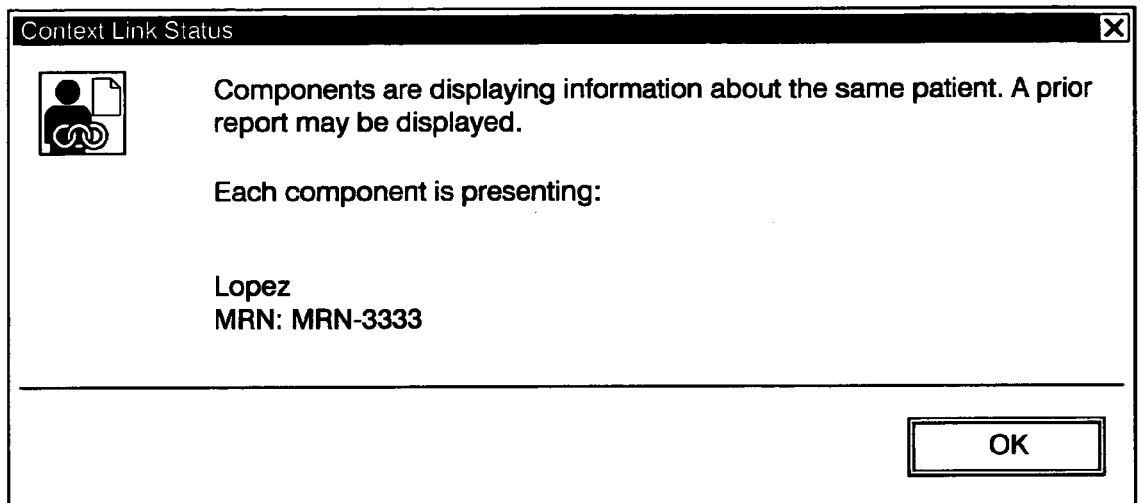
FIG. 9 illustrates one embodiment of a dialog box displaying detailed synchronization state information when applications are in a "prior report being viewed" scenario.

In the current embodiment, it is then possible to double click on the "prior report being viewed" indicator 38 to display a dialog box explaining the icon status. FIG. 9 illustrates one embodiment of a dialog box 40 displaying detailed synchronization state information when applications are in a "prior report being viewed" scenario.

Figure 10:
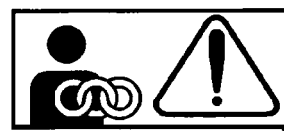
FIG. 10 illustrates one embodiment of an indicator displayed when context is indeterminate, specifically one embodiment of an "indeterminate" indicator.

FIG. 10 illustrates one embodiment of an indicator displayed when context is indeterminate, specifically one embodiment of an "indeterminate" indicator 42. The "indeterminate" indicator 42 indicates the indeterminate state. In one embodiment the "indeterminate" indicator 42 may be visible in the color yellow. The "indeterminate" indicator 42 in another embodiment may show an icon displaying a hazard type mark. Additionally, in another embodiment, the "indeterminate" indicator 42 may be visible in the color yellow and may also show an icon displaying a hazard type mark. Any number of color choices or icons may be used to indicate the "indeterminate" indicator 42.

Figure 11:
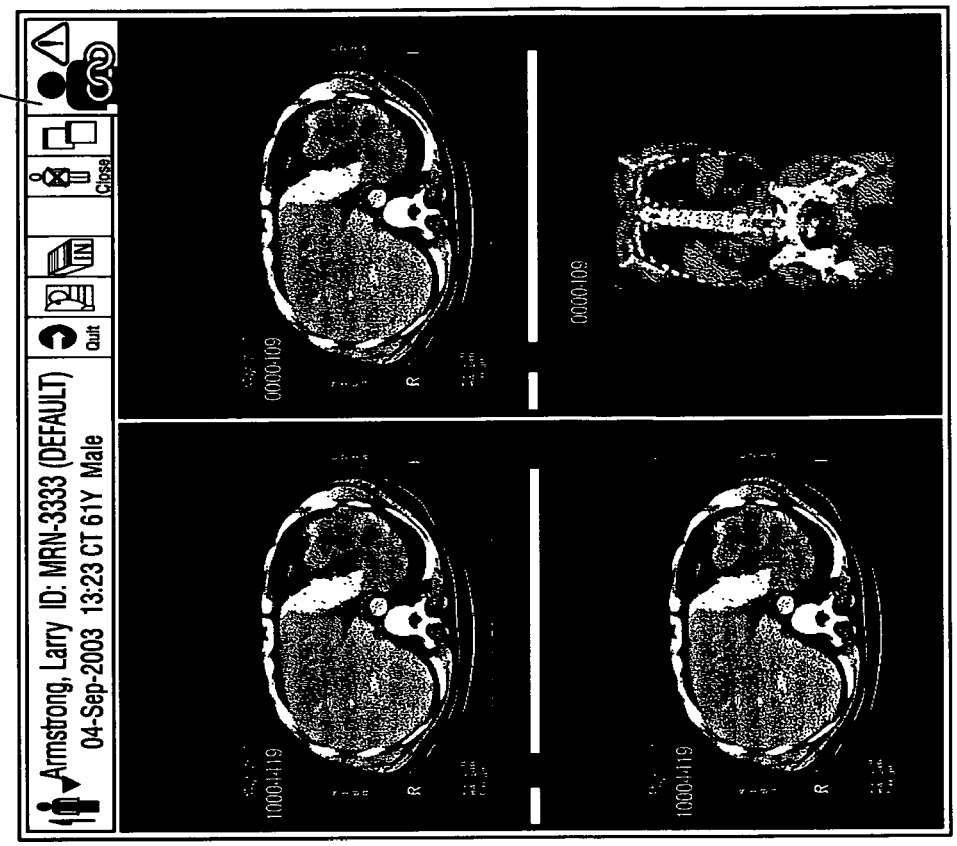
FIG. 11 illustrates screen shots of one embodiment showing two applications on a computer desktop that are in an unknown or indeterminate synchronization state with the "indeterminate" indicator in the top right-hand corner displaying the indeterminate state.

The "indeterminate" indicator 42 (See FIG. 10) may be displayed, for example, when in all visible applications, the patient MRN and last name matches (that is, critical data) but the accession numbers do not match (that is, non-critical data). FIG. 11 illustrates screen shots of one embodiment showing two applications on a computer desktop that are in an unknown or indeterminate synchronization state with the "indeterminate" indicator 42 in the top right-hand corner displaying the indeterminate state. In FIG. 11, both applications display a patient with the same MRN and last name. However, the accession number is different in each application.

Figure 12:
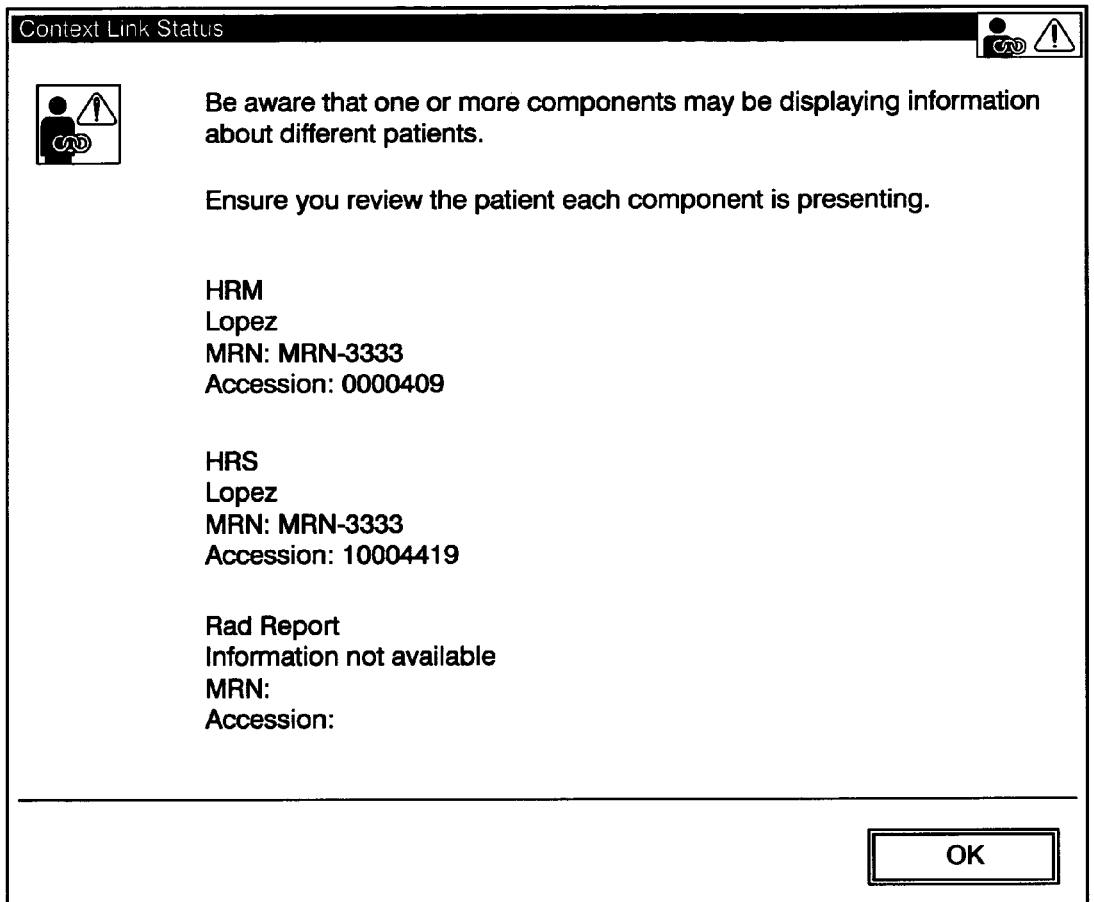
FIG. 12 illustrates one embodiment of a dialog box displaying detailed synchronization state information of each monitored application when the applications are in the indeterminate state.

In the current embodiment, it is then possible to double click on the "indeterminate" indicator 42 to display a dialog box explaining the icon status. FIG. 12 illustrates one embodiment of a dialog box 44 displaying detailed synchronization state information of each monitored application when the applications are in the indeterminate state.

Figure 13:
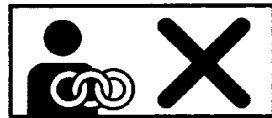
FIG. 13 illustrates one embodiment of an indicator displayed when context is not synchronized, specifically one embodiment of a "not synchronized" indicator.

FIG. 13 illustrates one embodiment of an indicator displayed when context is not synchronized, specifically one embodiment of a "not synchronized" indicator 46. The "not synchronized" indicator 46 indicates the not synchronized state. In one embodiment the "not synchronized" indicator 46 may be visible in the color red. The "not synchronized" indicator 46 in another embodiment may show an "X" mark. Additionally, in another embodiment, the "not synchronized" indicator 46 may be visible in the color red and may show an "X" mark. Any number of color choices or icons may be used to indicate the "not synchronized" indicator 46.

Figure 14:
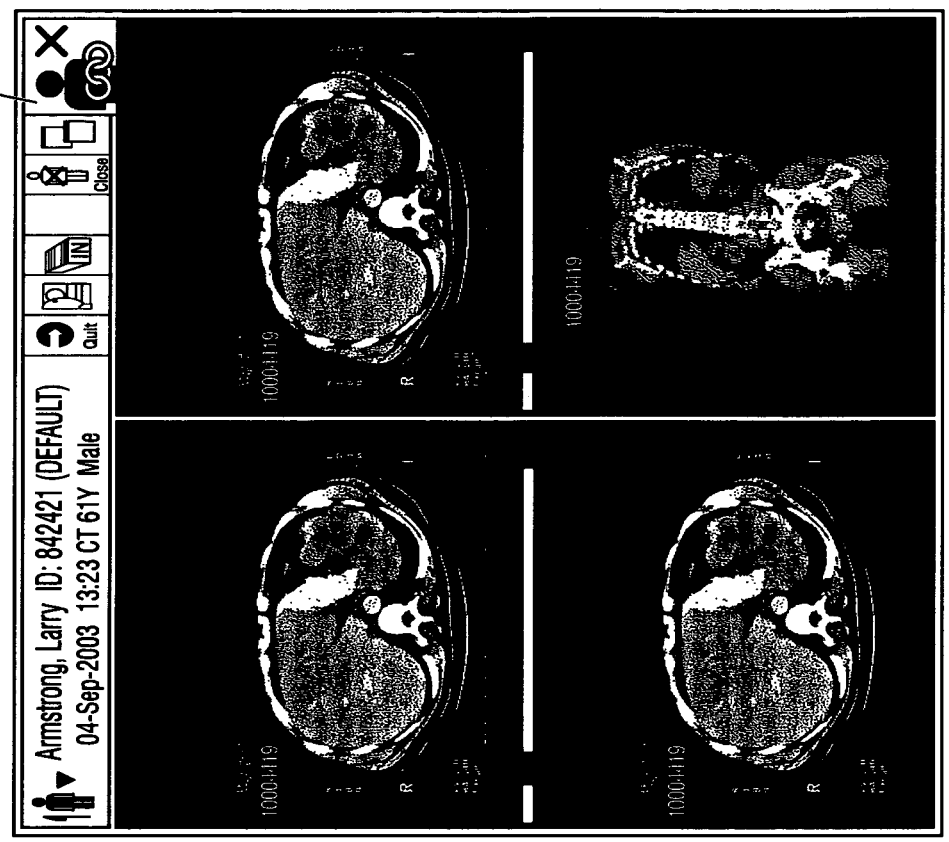
FIG. 14 depicts screen shots of one embodiment showing two applications on a computer desktop that are not synchronized with the "not synchronized" indicator in the top right-hand corner displaying the not synchronized state.

As previously discussed, the "not synchronized" indicator 46 (See FIG. 13) will be displayed when the visible applications are displaying critical data for different entities, that is, they are not synchronized. For example, if the patient's MRN number does not match in each of the visible applications, the "not synchronized" indicator will be displayed. FIG. 14 depicts screen shots of one embodiment showing two applications on a computer desktop that are not synchronized with the "not synchronized" indicator 46 in the top right-hand corner displaying the not synchronized state. In FIG. 14, each application displays a different patient.

Figure 15:
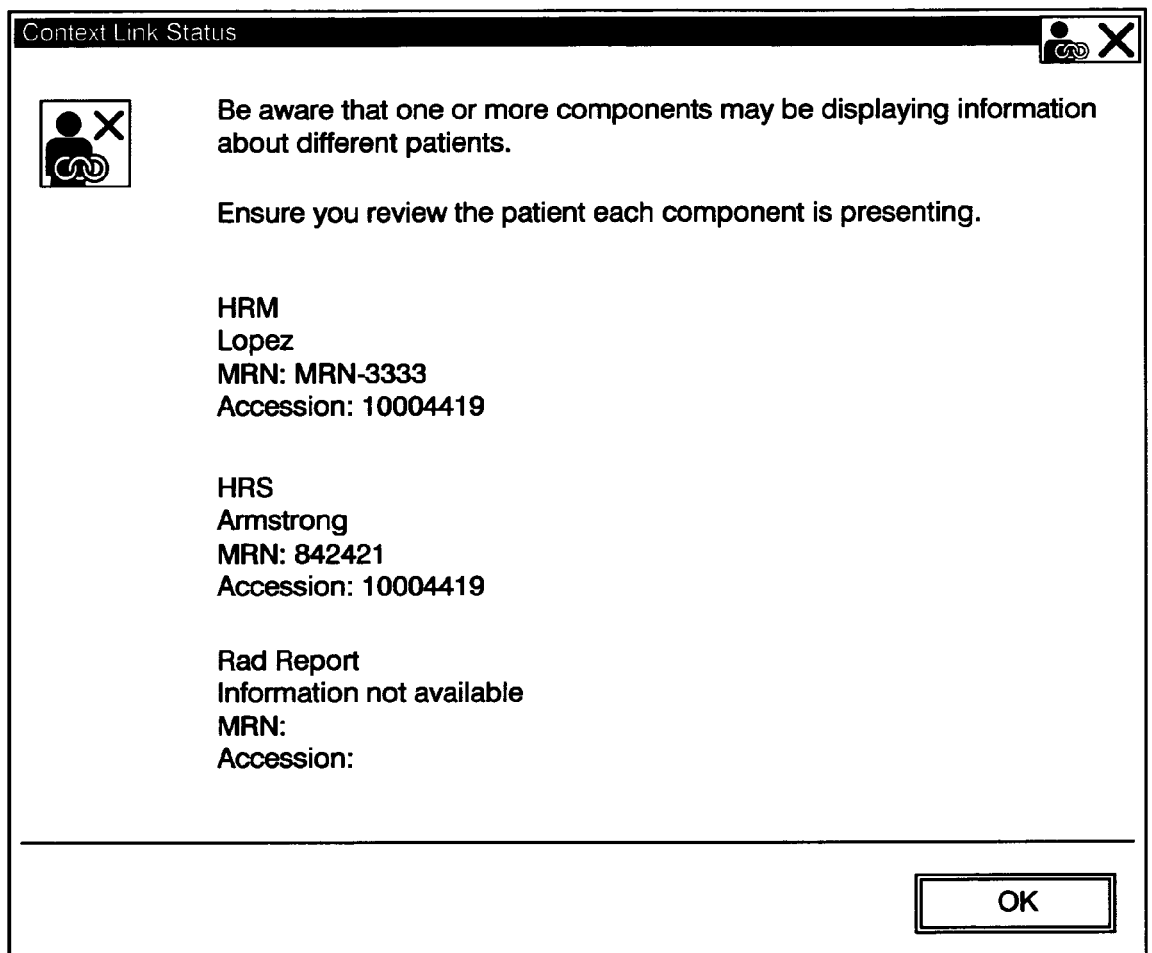
FIG. 15 illustrates one embodiment of a dialog box displaying detailed synchronization state information of each monitored application when the applications are in the not synchronized state.

In the current embodiment, it is then possible to double click on the "not synchronized" indicator 46 to display a dialog box explaining the icon status. FIG. 15 illustrates one embodiment of a dialog box 48 displaying detailed synchronization state information of each monitored application when the applications are in the not synchronized state.

In the current embodiment, an application, for example implemented using Microsoft Foundation Classes, watches particular preconfigured applications. Every two seconds, the application polls for the particular preconfigured applications and notes which patient (e.g., medical record number (MRN), last name) and study (e.g. accession) is being viewed in those particular applications. The application displays an indication to the user on the computer screen (via the indicator) as to whether or not the applications being watched are displaying information for the same patient. Those skilled in the art will appreciate that the application may be implemented in any number of languages or paradigms, as long as there is some way to display an indicator.

Further, in the current embodiment the indicator interacts with three (3) desktop applications. However, those skilled in the art will appreciate that the application may be configured to interact with many different applications as well as any number of desktop applications. More specifically, the indicator may retrieve information from an application in a variety of means. The manner in which the indicator retrieves information from an application is specific to the particular operating system and/or application that the present disclosure is interfacing with. The present disclosure interfaces with an application through an application interface. The present disclosure implements this interface in the present disclosure's getcontext method described above. It is worth noting that the getcontext method may take different forms as required to communicate with different applications. Three example techniques through which the indicator may retrieve information from an application are: (1) via an interface internal to the application; (2) via direct contact with and/or indirect "mining of" the application; and (3) via an interface external to the application. These three example techniques are described more fully below (and shown in FIG. 16). In one embodiment, all three example techniques may be used. However, these three example techniques do not provide a complete set of potential interfaces possible. Those skilled in the art will appreciate that many different interfaces may be used.

Figure 16:
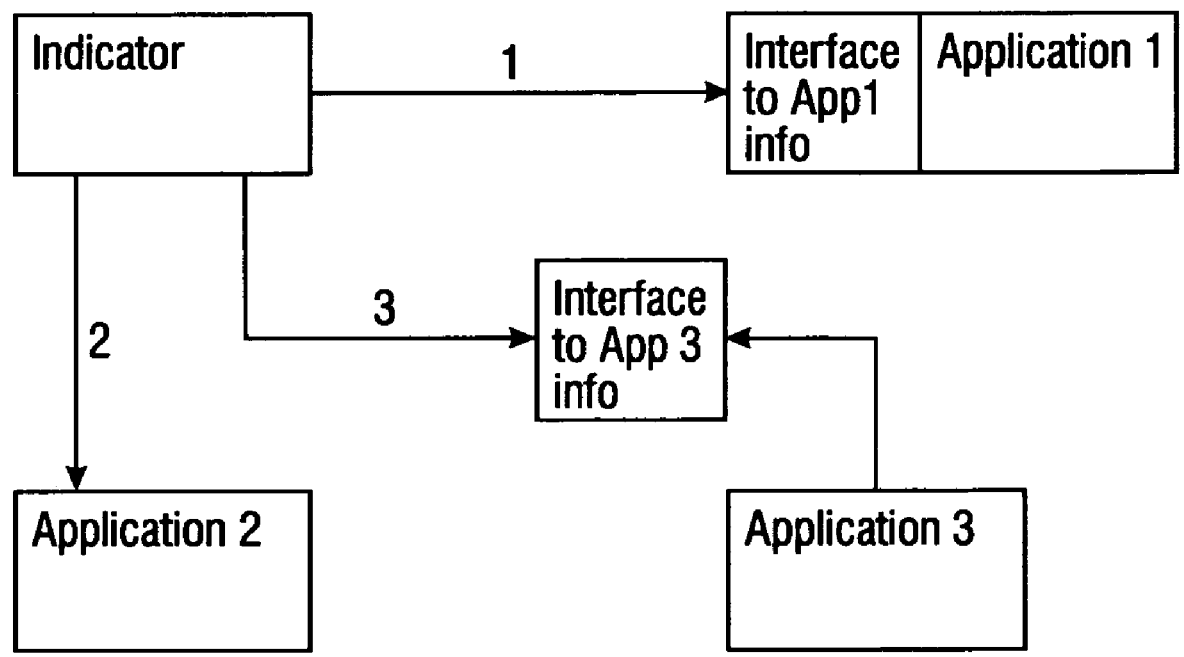
FIG. 16 illustrates one embodiment showing sample ways in which the indicator may retrieve information from various applications.

In the current embodiment, information may be first retrieved from one application, that is, from a first application, Application 1 as shown in FIG. 16, via an interface internal to the application. The indicator may determine if the first application's window is visible by asking the operating system to search for the first application's window, for example by window title. If the first application's window is visible, the indicator may connect to the first application via an internal interface. Methods on the internal interface may allow the indicator to extract from the first application information such as the current patient's name, MRN, etc. Additionally, the indicator may ask for any studies the first application has opened and may use methods to extract the opened anchor study's accession number. The anchor study is the study opened in the first application to be dictated/reported by the user.

In the current embodiment, information may be retrieved from another application, that is from a second application, Application 2 as shown in FIG. 16, via indirect "mining of" the application. The second application may be configured to write context information to its window title bar. For example, the second application may set the current patient's name, MRN, and study accession number to the second application's window title bar. The indicator may determine if the second application's window is visible by asking the Windows operating system to search for the second application's window (for example, by enumerating all windows and searching for constant parts of the window title). If the if the second application's window is visible, the indicator may parse the information in the title bar. That is, the indicator may retrieve information from the second application's window title bar.

Further, in the current embodiment, information may be retrieved from another application, that is, a third application, Application 3 as shown in FIG. 16, via an interface external to the application. The third application may be a web application. The indicator may determine if the third application's window is visible by asking the operating system to search for the third application's window (for example, by window title). If the third application's window is visible the indicator may retrieve the patient and study information from the third application's window via an external interface. The third application updates this external interface with the patient and study information whenever the third application changes its patient or study context.

The disclosure application does not require an application to notify a manager application when the application is going to change its context. The disclosure application removes this burden from any application that wants to change its context. When an application wishes to change its context, it may change it. The disclosure will discover the application's context change on its next poll or information retrieval step.

Additionally, prior art technology does not keep track of all application's states. The prior art technology acts as a repository for the current state's context values (e.g. the patient's medical record number). Unlike the prior technology that simply notifies applications of the current state or context values, the present disclosure can indicate the current context synchronization state—a single value that represents the context state, derived from examining all applications on the desktop. To determine the current context synchronization state with the prior art technology, a user would have to look closely at each application to see if each application is in-context. The disclosure saves the user from having to determine this value.

Additionally, with the prior art technology, on a system that has multiple integrated desktop applications, a user must know which application they are trying to interact with, and look at that application's icon to determine if it is safe to use that application (i.e., if it is in context). The disclosure removes the user's burden of having to find and look at a specific application to determine if it is in context. Instead, the user looks to a single consistent location, that is always available and visual, for the user interface.

Further, the present disclosure does not force applications to update their context, thus removing the complexities of applications handling unsaved data conditions. This also removes the burden of the user having to recall certain applications that are no longer participants in the context (because the user previously elected to break the application from the context). Finally, the present disclosure typically removes the burden of additional application programming to make it a participant in a synchronized desktop. This present disclosure improves physician/user confidence in using an integrated system.

The present disclosure indicates the synchronization state of all pre-configured application. However, the present disclosure may also run along-side applications participating in a CCOW or CCOW-like environment. In one embodiment in which the present disclosure is running along-side applications participating in a CCOW or CCOW-like environment, the present disclosure may continue to poll all preconfigured applications for their context state and provide a single visual indicator representing the synchronization state of the applications.

As previously discussed, automated synchronization is considered to be a benefit of running in a CCOW environment. However, when unsaved data conditions result and the user breaks applications from the shared context, it is up to the user to remember that some applications are no longer in context. At this point in the CCOW environment, the desktop has been returned to the original problem, that is, some applications are sharing context and some are not. It is at this point in the CCOW environment where the synchronization indicator of the present disclosure is useful. The user must ensure that applications are synchronized, for example, by manually synchronizing the application(s) with broken context or to rejoin the application(s) with broken context. That is, in the CCOW environment an application may supply a button in its user interface to force the application to re-join the shared context. The benefit of using the present disclosure indicator in the CCOW environment is that it indicates, with one quick glance, whether or not applications have been broken from the shared context. This is not currently possible in a CCOW-like environment without looking closely at each application.

While the present disclosure has been described in connection with preferred embodiments thereof, those of ordinary skill in the art will recognize that many modifications and variations are possible. The present invention is intended to be limited only by the following claims and not by the foregoing description which is intended to set forth the presently preferred embodiment.

What is claimed is:

1. A method, comprising:
retrieving identifying information from at least two software applications that are executed by a computing device, said identifying information identifying at least one individual about which the two software applications are currently causing display of medical information;
comparing the identifying information to determine whether the two software applications are currently causing display of medical information about the same individual;
generating a result indicative of said comparing;
determining, via the computing device, a synchronization state, among a plurality of predetermined synchronization states, based on the result, the determined synchronization state identifies a synchronization state of each of the two software applications while the two software applications are currently causing display of the identifying information;
associating the determined synchronization state with the result; and
displaying the result,
wherein a change in the display of the identifying information and corresponding medical information generated by one of the two software applications does not force a change in the display of the identifying information and corresponding medical information generated by the other software application,
wherein the identifying information is not exchanged between the two software applications.

2. The method of claim 1 wherein said retrieving includes directly interfacing with the at least two software applications.

3. The method of claim 1 wherein said retrieving includes indirectly interfacing with the at least two software applications.

4. The method of claim 1, additionally comprising defining the identifying information as critical or non-critical.

5. The method of claim 1 wherein retrieving occurs approximately every two seconds.

6. The method of claim 1 wherein the result includes one of synchronized, not synchronized, or indeterminate.

7. The method of claim 1 wherein the result is displayed in color.

8. The method of claim 1 wherein the result is displayed as an icon.

9. The method of claim 1 wherein the result is displayed as a link to additional information.

10. The method of claim 1 wherein the result is displayed in a consistent location.

11. A method for indicating context synchronization of applications on a computer comprising:
reading a configuration file to determine at least two software applications that are executed by a computing device;
reading a configuration file to determine identifying information to retrieve from said at least two software applications, said identifying information identifying at least one individual about which the two software applications are currently causing display of medical information;
retrieving identifying information from said at least two software applications;
comparing the identifying information to determine whether the two software applications are currently causing display of medical information about the same individual;
generating a result indicative of said comparing;
determining, via the computing device, a synchronization state, among a plurality of predetermined synchronization states, based on the result, the determined synchronization state identifies a synchronization state of each of the two software applications while the software applications are currently causing display of the identifying information;
associating the determined synchronization state with the result; and
displaying the result,
wherein a change in the display of the identifying information and corresponding medical information generated by one of the two software applications does not force a change in the display of the identifying information and corresponding medical information generated by the other software application,
wherein the identifying information is not exchanged between the two software applications.

12. The method of claim 11 wherein said retrieving includes directly interfacing with the at least two software applications.

13. The method of claim 11 wherein said retrieving includes indirectly interfacing with the at least two software applications.

14. The method of claim 11, additionally comprising defining the identifying information as critical or non-critical.

15. The method of claim 11 wherein retrieving occurs approximately every two seconds.

16. The method of claim 11 wherein the result includes one of synchronized, not synchronized, or indeterminate.

17. The method of claim 11 wherein the result is displayed in color.

18. The method of claim 11 wherein the result is displayed as an icon.

19. The method of claim 11 wherein the result is displayed as a link to additional information.

20. The method of claim 11 wherein the result is displayed in a consistent location.

21. A computer-readable storage medium storing computer-readable program code portions, the computer-readable program code portions comprising:
a first executable portion for retrieving identifying information from at least two software applications that are executed by a computing device, said identifying information identifying at least one individual about which the two software applications are currently causing display of medical information;
a second executable portion for comparing the identifying information to determine whether the two software applications are currently causing display of medical information about the same individual;
a third executable portion for generating a result indicative of said comparing;
a fourth executable portion for determining a synchronization state, among a plurality of predetermined synchronization states, based on the result, the determined synchronization state identifies a synchronization state of each of the two software applications while the two software applications are currently causing displaying of the identifying information;
a fifth executable portion for associating the determined synchronization state with the result; and a sixth executable portion for displaying the result,
wherein a change in the display of the identifying information and corresponding medical information generated by one of the two software applications does not force a change in the display of the identifying information and corresponding medical information generated by the other software application,
wherein the identifying information is not exchanged between the two software applications.

22. The computer-readable storage medium of claim 21 wherein said retrieving includes directly interfacing with the at least two software applications.

23. The computer-readable storage medium of claim 21 wherein said retrieving includes indirectly interfacing with the at least two software applications.

24. The computer-readable storage medium of claim 21, additionally comprising defining the identifying information as critical or non-critical.

25. The computer-readable storage medium of claim 21 wherein retrieving occurs approximately every two seconds.

26. The computer-readable storage medium of claim 21 wherein the result includes one of synchronized, not synchronized, or indeterminate.

27. The computer-readable storage medium of claim 21 wherein the result is displayed in color.

28. The computer-readable storage medium of claim 21 wherein the result is displayed as an icon.

29. The computer-readable storage medium of claim 21 wherein the result is displayed as a link to additional information.

30. The computer-readable storage medium of claim 21 wherein the result is displayed in a consistent location.

31. The method of claim 1, wherein the two software applications implement a Clinical Context Object Workgroup (CCOW) protocol.

32. The method of claim 1, wherein at least a portion of the two software applications are linked to each other.

33. The method of claim 1, wherein the medical information comprises first and second data and wherein a first software application of the applications causes display of the first data and a second software application of the applications causes display of the second data, and wherein the display of the first data and the display of the second data are independent of each other.

34. The method of claim 11, wherein the two software applications implement a Clinical Context Object Workgroup (CCOW) protocol.

35. The method of claim 11, wherein at least a portion of the two software applications are linked to each other.

36. The method of claim 11, wherein the medical information comprises first and second data and wherein a first software application of the applications causes display of the first data and a second software application of the applications causes display of the second data, and wherein the display of the first data and the display of the second data are independent of each other.

37. The computer-readable storage medium of claim 21, wherein the two software applications implement a Clinical Context Object Workgroup (CCOW) protocol.

38. The computer-readable storage medium of claim 21, wherein at least a portion of the two software applications are linked to each other.

39. The computer-readable storage medium of claim 21, wherein the medical information comprises first and second data and wherein a first software application of the applications causes display of the first data and a second software application of the applications causes display of the second data, and wherein the display of the first data and the display of the second data are independent of each other.

* * * * *